United States Patent
Zhu

(10) Patent No.: US 10,524,717 B2
(45) Date of Patent: Jan. 7, 2020

(54) DETECTION DEVICE AND FATIGUE DETECTION SYSTEM

(71) Applicant: BOE Technology Group Co., Ltd., Beijing (CN)

(72) Inventor: Lin Zhu, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/918,091

(22) Filed: Mar. 12, 2018

(65) Prior Publication Data

US 2019/0125237 A1    May 2, 2019

(30) Foreign Application Priority Data

Oct. 31, 2017    (CN) .......................... 2017 1 1045341

(51) Int. Cl.
*A61B 5/18* (2006.01)
*A61B 5/00* (2006.01)
(Continued)

(52) U.S. Cl.
CPC ............ *A61B 5/18* (2013.01); *A61B 5/02438* (2013.01); *A61B 5/103* (2013.01); *A61B 5/6843* (2013.01); *A61B 5/6893* (2013.01); *A61B 5/746* (2013.01); *B62D 1/046* (2013.01); *A61B 5/0245* (2013.01); *A61B 5/02055* (2013.01);
(Continued)

(58) Field of Classification Search
None
See application file for complete search history.

(56) References Cited

U.S. PATENT DOCUMENTS

| 2009/0212657 | A1* | 8/2009 | Mizuno | H02N 1/004 310/300 |
| 2010/0030429 | A1* | 2/2010 | Kuramori | B62D 1/046 701/42 |

(Continued)

FOREIGN PATENT DOCUMENTS

| CN | 103300869 A | 9/2013 |
| CN | 105547531 A | 5/2016 |

(Continued)

OTHER PUBLICATIONS

First Office Action, including Search Report, for Chinese Patent Application No. 201711045341.0, dated Nov. 12, 2019, 12 pages.

*Primary Examiner* — Leon Viet Q Nguyen
(74) *Attorney, Agent, or Firm* — Westman, Champlin & Koehler, P.A.

(57) ABSTRACT

Embodiments of the present disclosure provide a detection device. The detection device includes: a fixed member fixedly mounted to a target position; a first movable member arranged to face towards and in parallel with the fixed member, and movably connected to the fixed member by a first elastic member; at least one first electrode, having one end being fixed to the fixed member and the other end extending towards the first movable member along a first direction; and at least one second electrode, having one end being fixed to the first movable member and the other end extending towards the fixed member in a second direction, the second direction being parallel to the first direction. Embodiments of the present disclosure also provide a fatigue detection system.

15 Claims, 5 Drawing Sheets

(51) Int. Cl.
  *B62D 1/04* (2006.01)
  *A61B 5/024* (2006.01)
  *A61B 5/103* (2006.01)
  *A61B 5/0205* (2006.01)
  *A61B 5/0245* (2006.01)

(52) U.S. Cl.
  CPC ... *A61B 2562/0214* (2013.01); *B60Y 2400/30* (2013.01); *B62D 1/04* (2013.01)

(56) References Cited

U.S. PATENT DOCUMENTS

| | | | | |
|---|---|---|---|---|
| 2010/0107758 | A1* | 5/2010 | Kandori | B81B 3/0086 |
| | | | | 73/504.08 |
| 2012/0078122 | A1* | 3/2012 | Yokoyama | A61B 5/0245 |
| | | | | 600/484 |
| 2012/0230079 | A1* | 9/2012 | Li | H02N 1/008 |
| | | | | 365/145 |
| 2012/0293907 | A1* | 11/2012 | Jin | G01P 15/125 |
| | | | | 361/280 |
| 2015/0070941 | A1* | 3/2015 | Suzuki | H02M 3/34 |
| | | | | 363/19 |
| 2016/0216508 | A1* | 7/2016 | Tamamori | A61B 3/1015 |
| 2018/0170326 | A1* | 6/2018 | Wang | B60T 7/085 |

FOREIGN PATENT DOCUMENTS

| | | |
|---|---|---|
| CN | 107219026 A | 9/2017 |
| EP | 0 069 073 A1 | 1/1983 |
| WO | 2005/068960 A1 | 7/2005 |

\* cited by examiner

DETECTION DEVICE AND FATIGUE DETECTION SYSTEM

CROSS-REFERENCE TO RELATED APPLICATION

This application claims the benefit of Chinese Patent Application No. 201711045341.0 filed on Oct. 31, 2017 in the State Intellectual Property Office of China, the disclosure of which is incorporated herein by reference in entirety.

BACKGROUND

Technical Field

Embodiments of the present disclosure relate to the field of detection and the field of vehicle driving, and in particular, to a detection device and a fatigue detection system.

Description of the Related Art

A vehicle assistant driving system generally includes a road condition detection device, a vehicle condition detection device and a driver status detection device. The driver status detection device is used for detecting various physiological parameters of a driver, for example, detecting gazing direction, drowsiness, fatigue, and the like.

The fatigue detection refers to a detection device for detecting such as a gripping force applied on a steering wheel and a temperature. A gripping force sensor determines a deformation of an elastic body by detecting a change of an electric capacity to gain the gripping force acting on the elastic body, which has requirements on the material of the elastic body, and has a problem of lower detection accuracy.

SUMMARY

In view of this, embodiments of the present disclosure provide a detection device and a fatigue detection system for at least partially improving the detection accuracy.

The detection device according to an embodiment of the present disclosure includes:

a fixed member fixedly mounted to a target position;

a first movable member arranged to face towards and in parallel with the fixed member, and movably connected to the fixed member by a first elastic member;

at least one first electrode, having one end being fixed to the fixed member and the other end extending towards the first movable member along a first direction; and at least one second electrode, having one end being fixed to the first movable member and the other end extending towards the fixed member in a second direction, the second direction being parallel to the first direction.

As an optional solution, the detection device further includes:

a second movable member, at least one end of the second movable member being fixed; and at least one third electrode fixed to the second movable member.

As an optional solution, the third electrode and the first electrode or the second electrode constitute a variable area type capacitor.

As an optional solution, an insulation layer is provided between the third electrode and the first electrode or between the third electrode and the second electrode.

As an optional solution, the third electrode and the first electrode constitute a variable distance type capacitor.

As an optional solution, the second movable member extends in a third direction perpendicular to the first direction.

As an optional solution, second elastic members are provided on either end of the second movable member respectively.

As an optional solution, the second movable member extends in a fourth direction parallel to the first direction.

The fatigue detection system according to an embodiment of the present disclosure includes:

the detection device according to any one of the above embodiments, mounted on a steering wheel of a vehicle;

a driving device configured for supplying an electrode driving signal to the detection device based on a predetermined driving instruction; and a processing device configured for calculating a force acting on the detection device on a basis of a detection signal received from the detection device.

As an optional solution, the processing device is further configured to compare the calculated force with a predetermined threshold range, and the system further comprises:

an alarm device configured for sending an alarm signal when it is determined by the processing device that the calculated force exceeds the predetermined threshold range.

As an optional solution, the fatigue detection system further includes:

a temperature sensor mounted on a side of the detection device facing away from the steering wheel or at a position on the steering wheel adjacent to the detection device; and/or a heart rate sensor mounted on a side of the detection device facing away from the steering wheel or at a position on the steering wheel adjacent to the detection device.

DETAILED DESCRIPTION OF PREFERRED EMBODIMENTS

The embodiments of the present disclosure will be described in detail below with reference to the accompanying drawings.

Figure 1:
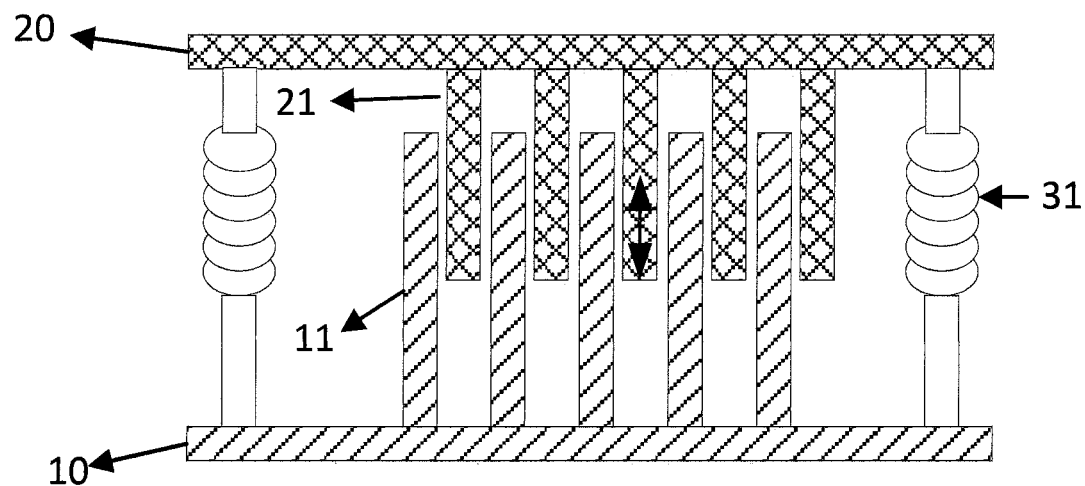
FIG. 1 is a schematic structural view of a detection device according to an embodiment of the present disclosure.

FIG. 1 is a schematic structural view of a detection device according to an embodiment of the present disclosure.

As shown in FIG. 1, the detection device according to the embodiment of the present disclosure includes a fixed member 10 and a first movable member 20 arranged to face towards and in parallel with each other, and a first elastic member 31 connected between the fixed member 10 and the first movable member 20. The first elastic member 31 may be a part or the whole of a connection member connected between the fixed member 10 and the first movable member 20.

One side of the fixed member 10 is fixedly mounted to a target position. The target position is a position where an action force such as pressure applied by an object or an operator needs to be detected, for example, a position where a pressure of an object to be measured (for example, a weight of a measured object or an operation force to be measured) is applied, for example, at a steering wheel of a vehicle.

One or more first electrodes 11 are provided on a side of the fixed member 10 opposite to the mounting side. The first electrode 11 may be a strip-shaped electrode or a columnar electrode, one end of which is fixed to the fixed member 10 and the other end of which extends away from the fixed member 10, for example, the other end may extend towards the first movable member 20 which faces towards the fixed member 10 in a first direction perpendicular to a surface of the fixed member 10.

Both ends of the first movable member 20 may be connected to both ends of the fixed member 10 by the first elastic members 31 respectively. Since the fixed member 10 is fixed at the target position, if a pressure is applied to the first movable member 20 towards the fixed member 10, the first movable member 20 will be displaced towards the fixed member 10 under such a pressure and the first elastic members 31 at both ends will be compressed. If the pressure is removed, the first elastic member 31 will return to its original uncompressed state due to its own restoring force, thereby resetting the first movable member 20.

One or more second electrodes 21 are provided on a side of the first movable member 20 facing the fixed member 10. The second electrode 21 may be a strip-shaped electrode or a columnar electrode, one end of which is fixed to the first movable member 20 and the other end of which extends towards the fixed member 10, for example, the other end may extend towards the fixed member 10 in a second direction perpendicular to a surface of the first movable member 20.

In the detection device according to the embodiment of the present disclosure, the fixed member 10 and the first movable member 20 may be arranged to face towards and in parallel with each other, then the second direction may be parallel to the first direction, that is, the first electrode 11 and the second electrode 21 are parallel to each other. In the embodiment of the present disclosure, free ends of the first electrodes 11 and the second electrodes 21 may be staggered with respect to each other, that is, when no pressure is applied to the first movable member 20, the ends of the first electrodes 11 and the second electrodes 21 do not face each other; or may face each other to form one or more pairs of interdigital electrodes.

When no pressure is applied to the first movable member 20, the length of the interposing portion between the first electrode 11 and the second electrode 21 (or the overlapping portion between the first electrode 11 and the second electrode 12) may be zero or a predetermined length. As the pressure acting on the first movable member 20 towards the fixed member 10 increases, the first movable member 20 is gradually displaced towards the fixed member 10, the distance between the first movable member 20 and the fixed member 10 gradually decreases, the length of the interposing portion between the first electrode 11 and the second electrode 21 gradually increases from zero or the predetermined length so that a capacitance generated by the interposing portion of the electrodes changes as a function of the distance between the first movable member 20 and the fixed member 10. The variation of the distance between the first movable member 20 and the fixed member 10 can be detected by monitoring the variation of the capacitance of the interposing portion of the electrodes.

The calculation equation of the capacitance Cx generated by the interposing portion of the electrodes is as follows:

$$Cx = \varepsilon S / 4\pi k d \qquad \text{Equation 1}$$

Where $\varepsilon$ is an electric conductivity of a filling material between the electrodes, S is an area of the interposing portion of the electrodes, k is an electrostatic force constant, and d is a distance between the interdigital electrodes.

Figure 2:
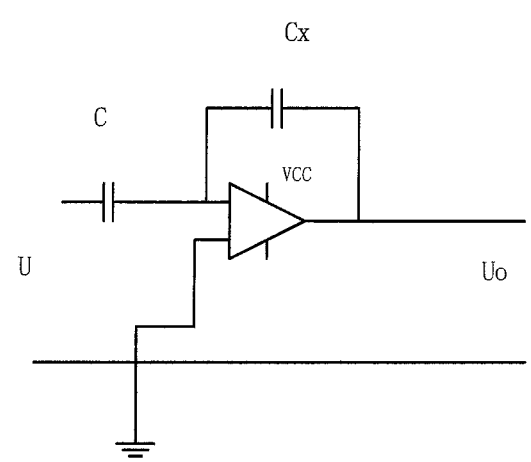
FIG. 2 is a schematic view of a detection parameter calculation circuit for a detection device according to an embodiment of the present disclosure.

The circuit for detecting the variation of the capacitance can be realized as for example an operational amplifier circuit shown in FIG. 2. As shown in FIG. 2, Cx is a capacitance formed by the interposing portion of the electrodes, an input voltage is inputted to an input end of the operational amplifier through a capacitor C, and an output voltage U0 is outputted to an output end of the operational amplifier, then the variation of Cx may be calculated according to the following Equation:

$$Cx = -C \times U / U0 \qquad \text{Equation 2}$$

Assuming that the width of the interposing portion of the electrodes is L0, the variation of the distance between the first movable member 20 and the fixed member 10 is $\Delta L$, then the increasing amount of area of the interposing portion of the electrodes is:

$$\Delta S = \Delta L \times L0 \qquad \text{Equation 3}$$

Since all the parameters except for the area S in the above capacitance calculation equation 1 are constant, the variation $\Delta Cx$ of the capacitance Cx is proportional to the variation $\Delta S$ of the area S, and the variation of the area may be determined according to the measured capacitance variation to calculate the variation of distance $\Delta L$. The variation of distance $\Delta L$ further corresponds to an amount of elastic deformation of the first elastic member 31. In combination with the elastic coefficient of the first elastic member 31, the magnitude of the pressure acting on the first movable member 20 can be obtained.

In addition to calculating the magnitude of the pressure in real time, a mapping relationship between the capacitance variation and the magnitude of pressure can be pre-determined and saved as a map so as to determine the magnitude of pressure directly through the measured capacitance variation.

By means of the detection device according to the embodiment of the present disclosure, it can accurately detect the magnitude of the acting force acting on the detection device and further accurately determine the force acting state of the object or the force acting state of the operator, thereby achieving a better effect in aspect of improving the pressure detection accuracy.

Figure 3:
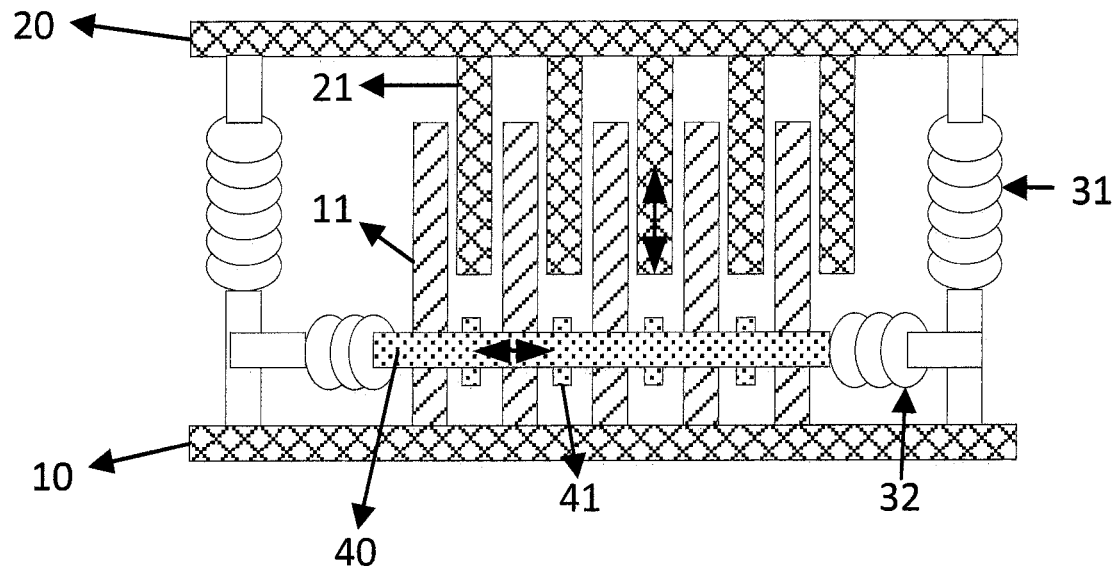
FIG. 3 is a schematic structural view of a detection device according to another embodiment of the present disclosure.
Figure 4:
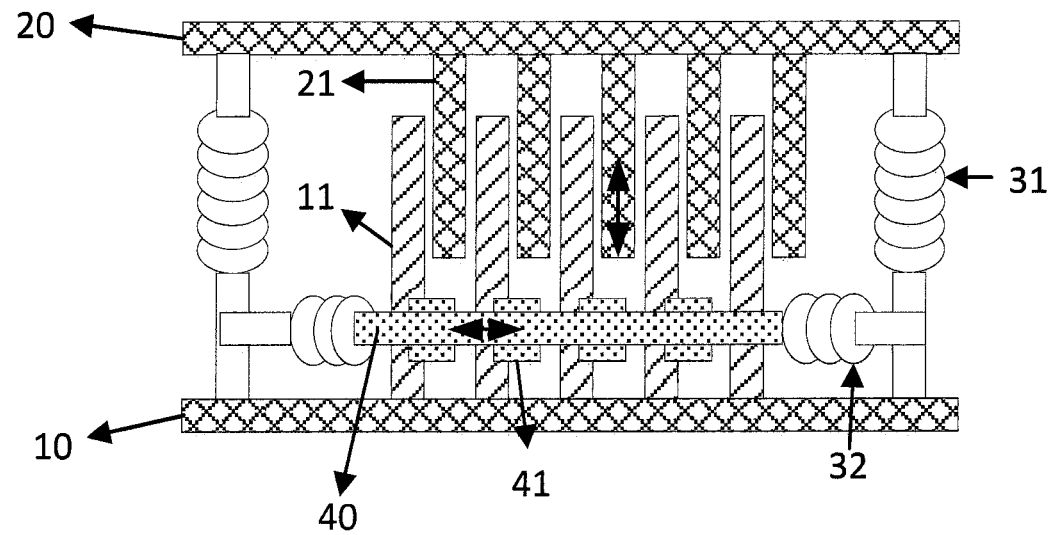
FIG. 4 is a schematic structural view of a detection device according to a further embodiment of the present disclosure.
Figure 5:
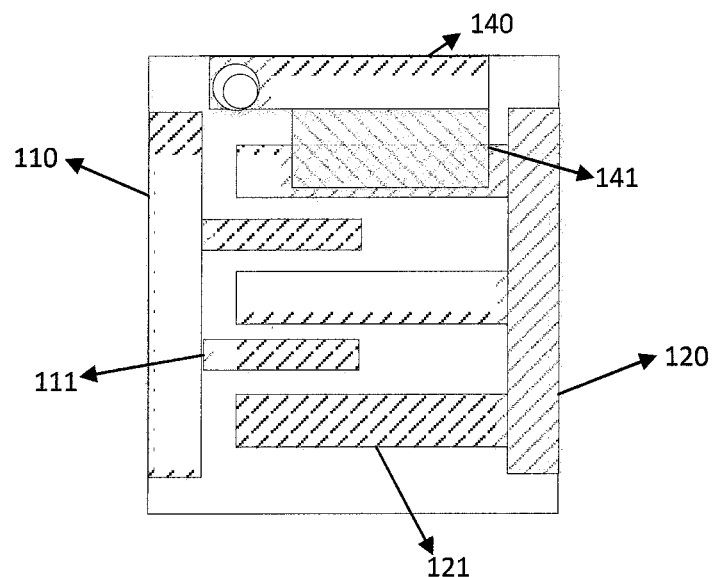
FIG. 5 is a schematic structural view of a detection device according to an embodiment of the present disclosure in one state.

FIGS. 3-5, in some embodiments of the present disclosure, the detection device may further include a second movable member 40 in addition to the fixed member 10 and the first movable member 20 shown in FIG. 1. The second movable member 40 may be fixed at one end or may be fixed at both ends. One or more third electrodes 41 may be provided on a side of the second movable member 40 facing the first electrodes 11, 111 or the second electrodes 21, 121. The third electrode 41 may be a strip-shaped electrode or a planar electrode, one end of which is fixed to the second movable member 40 and the other end of which extends towards the first electrodes 11, 111 or the second electrodes 21, 121.

In some embodiments of the present disclosure, the third electrode 41 and the first electrode 11, 111 or the second electrode 121 may constitute a variable area type capacitor, or the third electrode 41 and the first electrode 11 may constitute a variable distance type capacitor for detecting another acting force which is different from the acting force acting on the first movable member 20, 121.

Next, various embodiments of the detection device having the second movable member 40 will be described.

FIG. 3 is a schematic structural view of a detection device according to another embodiment of the present disclosure.

As shown in FIG. 3, the detection device further includes a second movable member 40 in addition to the fixed member 10 and the first movable member 20 shown in FIG. 1. The second movable member 40 extends in a third direction perpendicular to the first direction or the second direction (i.e., the extending direction of the first electrode 11 or the second electrode 21), and both ends of the second movable member 40 are fixedly connected. The connection manner may be as follows: if the first elastic member 31 is a part of the connection member connected between the fixed member 10 and the first movable member 20, then the both ends of the second movable member 40 may be connected to other portions of the connection member; alternatively, the both ends of the second movable member 40 are connected to other connection members provided on the fixed member 10 no matter whether the first elastic member 31 is a part of or the whole of the connection member connected between the fixed member 10 and the first movable member.

Again, in addition to the embodiment in which the both ends of the second movable member 40 shown in FIG. 3 are connected to the connection members among the connection members at the both ends of the first elastic members 31 close to the fixed member 10, the embodiments of the present disclosure may further include an embodiment in which the both ends of the second movable member 40 are connected to the connection members among the connection members at the both ends of the first elastic member 31 close to the first movable member 20.

One or more third electrodes 41 are provided on a side of the second movable member 40 facing the first electrodes 11 or the second electrodes 21. The third electrode 41 may be a strip-shaped electrode or a planar electrode, one end of which is fixed to the second movable member 40 and the other end of which extends towards the first electrodes 11 or the second electrodes 21.

Second elastic members 32 are provided on both ends of the second movable member 40. If an acting force is applied to the second movable member 40 in the longitudinal direction of the second movable member, the second movable member 40 is displaced towards one end thereof to compress the second elastic member 32 connected to this end of the second movable member or stretch the second elastic member 32 connected to the other end of the second movable member.

As shown in FIG. 3, the free end of the third electrode 41 extends towards the first electrode 11, and the free end of the third electrode 41 may extend to face a side surface of the first electrode 11.

If the second movable member 40 is displaced towards one end thereof to compress the second elastic member 32 connected to this end of the second movable member, the third electrode 41 disposed on the second movable member 40 is driven to move close to the first electrode 11 or away from the first electrode 11, therefore, the third electrode 41 disposed on the second movable member 40 and configured as described above and the first electrode 11 constitute a variable distance type capacitor.

In the embodiment shown in FIG. 3, the facing area S between the electrodes of the capacitor constituted by the third electrode 41 and the first electrode 11 is constant. According to the Equation 1, the variation of capacitance is inversely proportional to the variation of distance between electrodes. Assuming that the variation of distance between the third electrode 41 and the first electrode 11 is $\Delta d$, the variation of capacitance $\Delta C_x$ may be measured according to the operational amplifier circuit shown in FIG. 2 and the Equation 2, then the variation of distance $\Delta d$ may be calculated from the Equation 1. The variation of distance $\Delta d$ further corresponds to the amount of elastic deformation of the second elastic member 32. In combination with the elastic coefficient of the second elastic member 32, the magnitude of the acting force acting on the second movable member 40 in the longitudinal direction thereof can be obtained.

In the embodiments of the present disclosure, the interaction between the various electrodes is fully utilized by one detection device, so that magnitude of different acting forces acting on the detection device can be detected with fewer members, thereby achieving a good force measuring effect.

FIG. 4 is a schematic structural view of a detection device according to a further embodiment of the present disclosure.

The embodiment shown in FIG. 4 differs from the embodiment shown in FIG. 3 in the arrangement of the third electrode 41. As shown in FIG. 4, the third electrode 41 is disposed at a distance from the first electrode 11. If the second movable member 40 is displaced towards one end thereof to compress the second elastic member 32 connected to this end of the second movable member, the third electrode 41 disposed on the second movable member 40 is driven to move in a direction such that the facing area between the third electrode and the first electrode 11 becomes larger or the facing area between the third electrode and the first electrode 11 becomes smaller, therefore, the third electrode 41 disposed on the second movable member 40 and configured as described above and the first electrode 11 constitute a variable area type capacitor.

In the embodiment shown in FIG. 4, the distance d between the electrodes of the capacitor constituted by the third electrode 41 and the first electrode 11 is constant. According to the Equation 1, the variation of capacitance is inversely proportional to the variation of facing area between electrodes. Assuming that the variation of facing area between the third electrode 41 and the first electrode 11 is $\Delta S$, the variation of capacitance $\Delta C_x$ may be measured according to the operational amplifier circuit shown in FIG. 2 and the Equation 2, then the variation of facing area $\Delta S$ may be calculated from the Equation 1, and the amount of displacement of the second movable member 40 may be calculated from the length of the third electrode 41. The amount of displacement further corresponds to the amount of elastic deformation of the second elastic member 32. In combination with the elastic coefficient of the second elastic member 32, the magnitude of the acting force acting on the second movable member 40 in the longitudinal direction thereof can be obtained.

Figure 6:
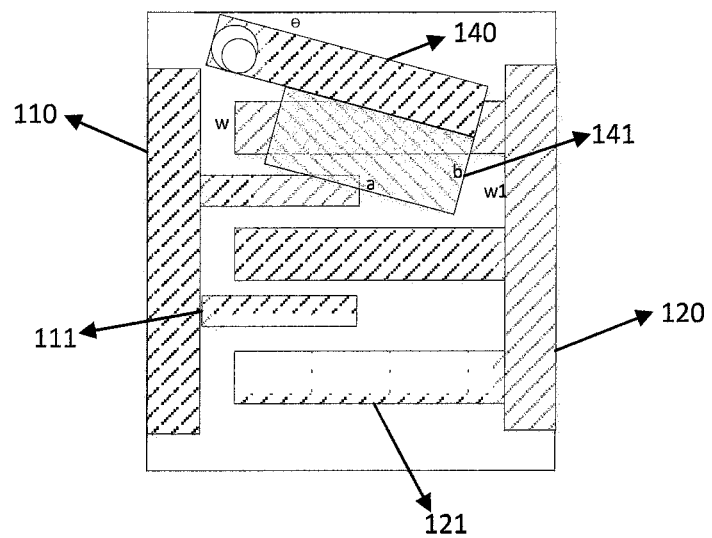
FIG. 6 is a schematic structural view of the detection device shown in FIG. 5 in another state.

FIG. 5 is a schematic structural view of a detection device according to an embodiment of the present disclosure in one state; FIG. 6 is a schematic structural view of the detection device shown in FIG. 5 in another state.

In the detection device of FIG. 5, the fixed member 110, the first electrode 111, the first movable member 120 and the second electrode 121 are the same as the fixed member 10, the first electrode 11, the first movable member 20 and the second electrode 21 in the embodiment shown in FIG. 1. It should be noted here that, in FIG. 5, for the sake of simplicity of illustration, the elastic member connected between the fixed member 110 and the first movable member 120 (corresponding to the first elastic member 31 in the embodiment shown in FIG. 1) is omitted.

As shown in FIG. 5, a second movable member 140 is provided on one end side of the fixed member 110 and the first movable member 120 facing each other and arranged in parallel with each other, and the second movable member extends in a fourth direction parallel to the first direction or the second direction (i.e., the extending direction of the first electrode 111 or the second electrode 121). One end of the second movable member 140 is fixed by for example an elastic member which is elastically deformable in a circumferential direction. If a force is applied to the second movable member 140 towards the first electrode 111 or the second electrode 121, the second movable member 140 rotates around its fixed end by a certain angle θ so that the facing area between it and the first electrode 111 or the second electrode 121 changes, thereby a third electrode 141 and the first electrode 111 or the second electrode 121 constitute a variable area type capacitor, as shown in FIG. 6. It should be noted that the facing position between the electrodes shown in FIG. 6 is only exemplary, and the facing position may be determined in actual application according to requirements.

The relationship between the variation of capacitance and the rotation angle θ can be obtained in advance by calculation, and the magnitude of the acting force can be determined according to the relationship between the rotation angle θ and the acting force. As shown in FIG. 6, assuming that a width of the second electrode 121 is w, the distance between the second electrodes 121 is w1, and the lengths of the sides of the third electrode 141 are a and b respectively, the facing area between the third electrode 141 and one of the second electrodes 121 closest to the third electrode 141 is:

$$S = a \times b \times \sin\theta \qquad \text{Equation 4}$$

The relationship between the variation of capacitance and the variation of area can be determined according to the Equation 1, and further the relationship between the variation of capacitance and the variation of rotation angle can be determined, and then according to the elastic torsion coefficient of the elastic member at the fixed end of the second movable member, the relationship between the variation of rotation angle and the acting force may be determined, and finally the magnitude of the acting force may be obtained.

Figure 7:
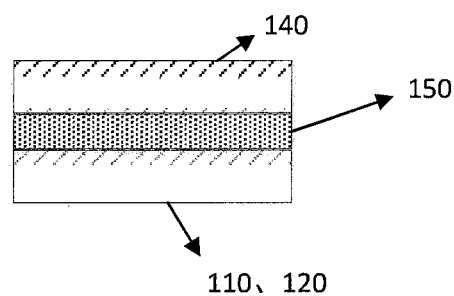
FIG. 7 is a schematic cross-sectional view of a detection device according to an embodiment of the present disclosure.

In an embodiment of the present disclosure, when the third electrode and the first electrode or the second electrode constitute a variable area type capacitor, an insulation layer 150 may be provided between the third electrode 41, 141 and the first electrode 11, 111 or the second electrode 21, 121, as shown in FIG. 7, so as to reduce an error of the distance between the third electrode and the first electrode or the second electrode.

Figure 8:
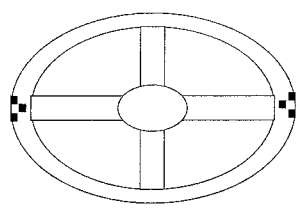
FIG. 8 is a schematic view of an arrangement of a detection device applied to a steering wheel according to an embodiment of the present disclosure.

FIG. 8 is a schematic view of an arrangement of a detection device applied to a steering wheel according to an embodiment of the present disclosure.

As shown in FIG. 8, the detection device shown in FIGS. 1-7 can be applied to a steering wheel of a vehicle, for example, mounted in a position on the steering wheel which is normally held by both hands. The mounting method is as follows: the detection device is mounted on the periphery of the steering wheel, and the fixing surface of the fixed member 10, 110 of the detection device is fixed at a target position of the steering wheel, so that the hands of the driver can just be made in contact with the detection device when the hands hold the steering wheel. In this way, the gripping force of the palm and the degree of attachment of the palm may be detected.

Figure 9:
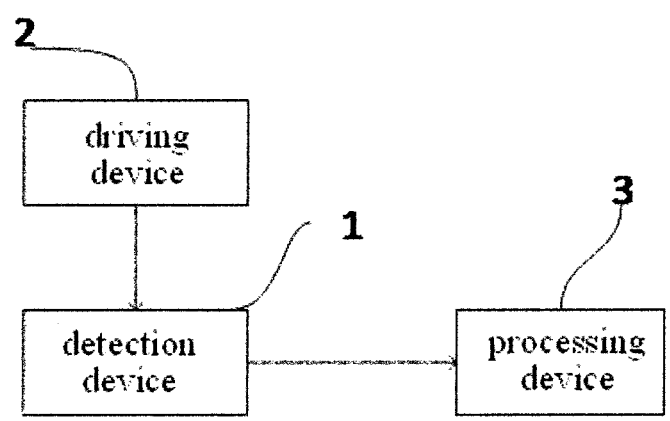
FIG. 9 is a schematic block diagram of a fatigue detection system according to an embodiment of the present disclosure.

FIG. 9 is a schematic block diagram of a fatigue detection system according to an embodiment of the present disclosure.

As shown in FIG. 9, the fatigue detection system according to the embodiment of the present disclosure includes a detection device 1, a driving device 2, and a processing device 3.

The detection device 1 includes any one of the above-described detection devices according to the embodiments of the present disclosure and is mounted on a steering wheel of a vehicle as shown in FIG. 8. The detection device 1 may further include a capacitance detection circuit as shown in FIG. 2.

The driving device 2 is configured for supplying an electrode driving signal to the detection device 1 based on a predetermined driving instruction. If the detection device 1 is a detection device including a second movable member according to the embodiment of the present disclosure, capacitors are formed between the first electrode and the second electrode, and between the third electrode and the first electrode or the second electrode. Therefore, when detecting the capacitances, the driving device 2 cannot supply electrical power to all the electrodes at the same time, one detection period T can be allocated to two driving signals and controlled by a clock signal. During the period T×D, one driving signal is applied to the capacitor constituted by the first electrode and the second electrode, and during the period T×(1−D), the other driving signal is applied to the capacitor constituted by the third electrode and the first electrode or the second electrode.

The processing device 3 is configured for calculating a force acting on the detection device on a basis of a detection signal received from the detection device 1.

With the fatigue detection system according to the embodiments of the present disclosure, the acting force applied by the driver to the steering wheel can be accurately detected, facilitating detecting the fatigue state of the driver.

Figure 10:
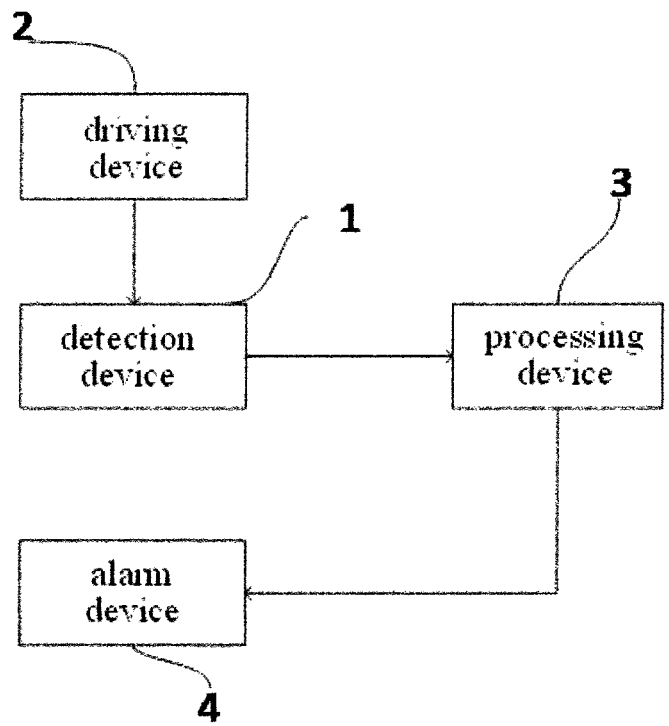
FIG. 10 is a schematic block diagram of a fatigue detection system according to another embodiment of the present disclosure.

FIG. 10 is a schematic block diagram of a fatigue detection system according to another embodiment of the present disclosure.

As shown in FIG. 10, the fatigue detection system according to the embodiment of the present disclosure further includes an alarm device 4, and the processing device 3 is configured to compare the calculated force with a predetermined threshold range. If the calculated force exceeds the threshold range in the comparison, it sends an instruction signal to the alarm device 4, and the alarm device 4 sends an audible and visual alarm signal or an intelligent alarm voice when receiving the instruction signal. For example, if the calculated force is small, it is determined that the driver is in a state of fatigue or the steering wheel is not held, and the corresponding alarm may be made; if the calculated force is large, it is determined that the driver is nervous or in a state of drowsiness, and the corresponding alarm is also made.

Figure 11:
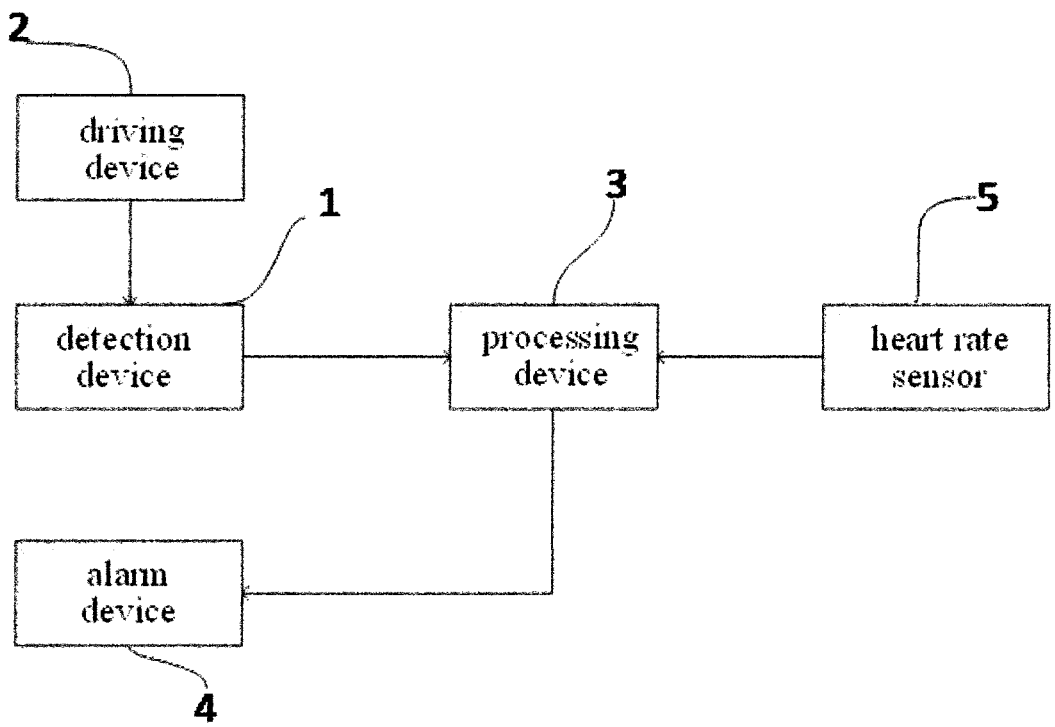
FIG. 11 is a schematic block diagram of a fatigue detection system according to a further embodiment of the present disclosure.

FIG. 11 is a schematic block diagram of a fatigue detection system according to a further embodiment of the present disclosure.

As shown in FIG. 11, the fatigue detection system according to the embodiment of the present disclosure may further include a heart rate sensor 5 which may be mounted on a side of the detection device facing away from the steering wheel or may be mounted at a position on the steering wheel adjacent to the detection device. In addition to the heart rate sensor 5, the fatigue detection system according to the embodiment of the present disclosure may further include a temperature sensor which may also be mounted on a side of the detection device facing away from the steering wheel or may be mounted at a position on the steering wheel adjacent to the detection device. By means of the fatigue detection system according to the embodiment of the present disclosure, it can comprehensively detect various physiological states of the driver and can facilitate accurately determining the driver's current state so as to perform effective fatigue detection.

According to the detection scheme of the embodiments of the present disclosure, the acting force acting on the detection device can be accurately detected, and the current fatigue state of the driver can be accurately determined, thereby achieving a better effect in aspect of fatigue detection.

Various embodiments of the present disclosure have been described above, but the present disclosure is not limited to the above specific embodiments. Various variations and modifications may be made to the foregoing embodiments by those skilled in the art without departing from the scope of the present disclosure, and such variations and modifications fall within the scope of the present disclosure as claimed.

What is claimed is:

1. A detection device, comprising:
   a fixed member fixedly mounted to a target position;
   a first movable member arranged to face towards and in parallel with the fixed member, and movably connected to the fixed member by a first elastic member;
   at least one first electrode, having one end being fixed to the fixed member and the other end extending towards the first movable member along a first direction; and
   at least one second electrode, having one end being fixed to the first movable member and the other end extending towards the fixed member in a second direction, the second direction being parallel to the first direction,
   wherein the detection device is configured to detect a variation of a distance between the first movable member and the fixed member,
   wherein the detection device further comprises:
      a second movable member, at least one end of the second movable member being fixed; and
      at least one third electrode fixed to the second movable member,
   wherein the first elastic member is a part of a connection member connected between the fixed member and the first movable member,
   wherein the at least one third electrode is disposed on a side of the second movable member facing the first electrode or the second electrode, one end of the at least one third electrode is fixed to the second movable member and the other end of the at least one third electrode extends towards the first electrode or the second electrode,
   wherein both ends of the second movable member are connected to the other part of said connection member.

2. The detection device according to claim 1, wherein the third electrode and the first electrode or the second electrode constitute a variable area type capacitor.

3. The detection device according to claim 2, wherein an insulation layer is provided between the third electrode and the first electrode or between the third electrode and the second electrode.

4. The detection device according to claim 1, wherein the third electrode and the first electrode constitute a variable distance type capacitor.

5. The detection device according to claim 1, wherein the second movable member extends in a third direction perpendicular to the first direction.

6. The detection device according to claim 5, wherein second elastic members are provided on either end of the second movable member respectively.

7. The detection device according to claim 1, wherein the second movable member extends in a fourth direction parallel to the first direction.

8. The detection device according to claim 2, wherein the second movable member extends in a third direction perpendicular to the first direction.

9. The detection device according to claim 3, wherein the second movable member extends in a third direction perpendicular to the first direction.

10. The detection device according to claim 4, wherein the second movable member extends in a third direction perpendicular to the first direction.

11. The detection device according to claim 2, wherein the second movable member extends in a fourth direction parallel to the first direction.

12. A fatigue detection system, comprising:
   the detection device according to claim 1, mounted on a steering wheel of a vehicle;
   a driving device configured for supplying an electrode driving signal to the detection device based on a predetermined driving instruction; and
   a processing device configured for calculating a force acting on the detection device on a basis of a detection signal received from the detection device.

13. The fatigue detection system according to claim 12, wherein the processing device is further configured to compare the calculated force with a predetermined threshold range, and the system further comprises:
   an alarm device configured for sending an alarm signal when it is determined by the processing device that the calculated force exceeds the predetermined threshold range.

14. The fatigue detection system according to claim 12, further comprising:
   a temperature sensor mounted on a side of the detection device facing away from the steering wheel or at a position on the steering wheel adjacent to the detection device; and/or a heart rate sensor mounted on a side of the detection device facing away from the steering wheel or at a position on the steering wheel adjacent to the detection device.

15. The fatigue detection system according to claim 13, further comprising:
a temperature sensor mounted on a side of the detection device facing away from the steering wheel or at a position on the steering wheel adjacent to the detection device; and/or
a heart rate sensor mounted on a side of the detection device facing away from the steering wheel or at a position on the steering wheel adjacent to the detection device.

* * * * *